United States Patent [19]

King

[11] Patent Number: Plant 6,284

[45] Date of Patent: Sep. 13, 1988

[54] *LIBOCEDRUS PLUMOSA* 'SONRISE'

[76] Inventor: Stephen T. King, 132 Victory Rd., Laingholm, Auckland 7, New Zealand

[21] Appl. No.: 648,783

[22] Filed: Sep. 10, 1984

[51] Int. Cl.[4] ..... A01H 7/00

[52] U.S. Cl. ..... Plt./50

[58] Field of Search ..... Plt./50

[56] References Cited

U.S. PATENT DOCUMENTS

P.P. 3,839 3/1976 Swane ..... Plt. 50

OTHER PUBLICATIONS

The Legal Aspects of Plant Tissue Culture and Patents, Bagwill, Environmental and Experimental Botany, vol. 21, No. 3/4, pp. 383–387, 1981.

*Primary Examiner*—Robert E. Bagwill

[57] ABSTRACT

A variety of *Libocedrus plumosa* having yellow foliage when grown in full sun.

1 Drawing Sheet

ORIGIN

Selected from seedlings I propagated in my nursery. The seed was collected from a tree typical of the species located in natural indigenous rainforest.

The 'Sonrise' variety differs by foliage colour being yellow when in open sun, as shown in the drawings, and corresponds to Royal Horticultural Society Colour Chart Yellow Group 9B.

BOTANICAL DESCRIPTION

Corresponds to the standard text description of *Libocedrus plumosa* (D.Don) Sargent, Silva. N. Amer. 10 1896, 134 described in Flora of New Zealand, H. H. Allan 1961; viz.

Tree up to 25 m., trunk up to 12 dm diameter., bark falling in narrow thin strips. Branchlets distichous, of juveniles flattened, up to 7 mm broad; of adults less compressed up to 3 mm broad.

Leaves quadrifarious, lateral up to 5 mm long, connate, sheathing, spreading; dorsal and ventral up to 2.5 mm long, triangular, subappressed. Male strobili 5–8 mm long, linear; sporophylls 8–12, apiculus thin, ovate.

Female cones ovoid 1–1.5 cm long of 4 carpidia with projecting dorsal curved mucro. Seeds 2.

I claim:

1. A new and distinct variety of *Libocedrus plumosa* named Sonrise substantially as described and illustrated, characterised by its bright yellow foliage colour when grown in full sun.

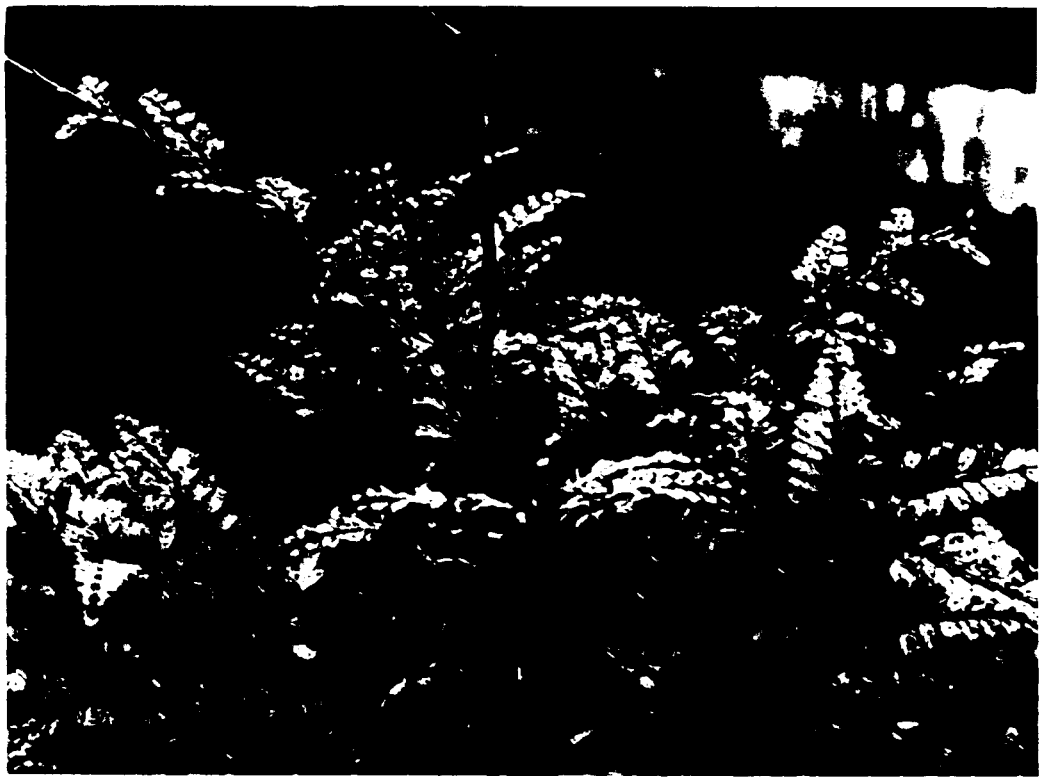
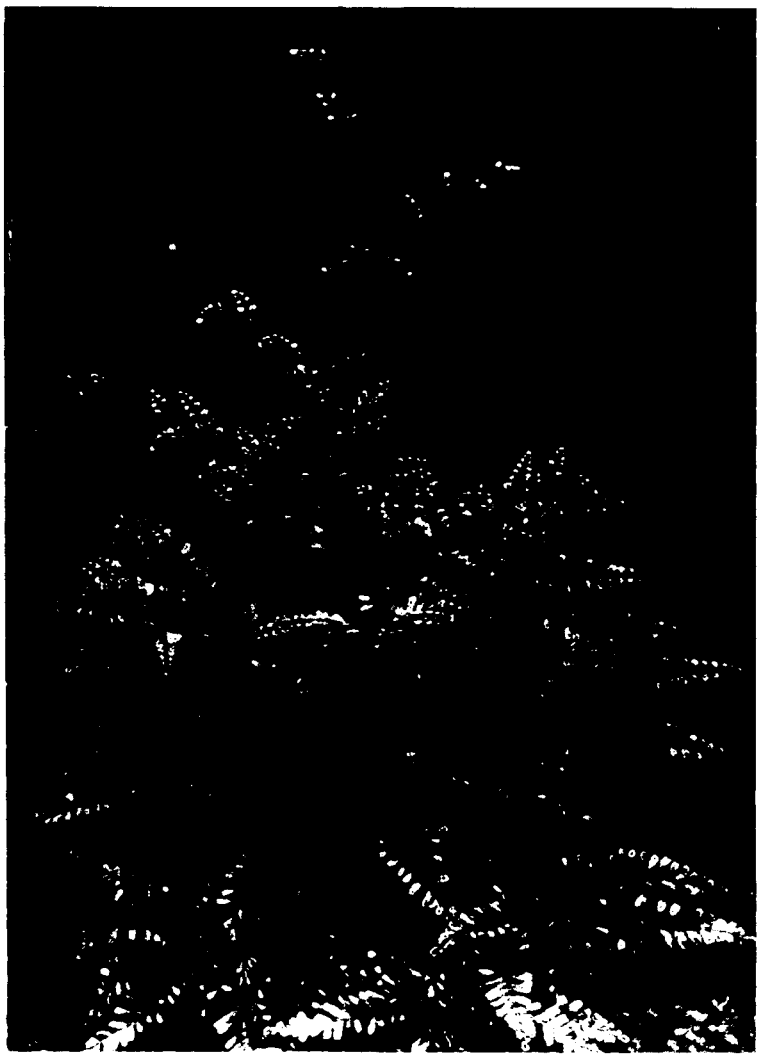

* * * * *